US011432761B1

(12) United States Patent
Lee et al.

(10) Patent No.: US 11,432,761 B1
(45) Date of Patent: Sep. 6, 2022

(54) METHOD AND SERVER FOR DEMENTIA TEST BASED ON VOICE QUESTION AND ANSWER USING ARTIFICIAL INTELLIGENCE CALL

(71) Applicant: SEVENPOINTONE INC., Seoul (KR)

(72) Inventors: Hyeonjun Lee, Seoul (KR); Juyeong Yoo, Siheung-si (KR)

(73) Assignee: SEVENPOINTONE INC., Seoul (KR)

( * ) Notice: Subject to any disclaimer, the term of this patent is extended or adjusted under 35 U.S.C. 154(b) by 0 days.

(21) Appl. No.: 17/749,867

(22) Filed: May 20, 2022

Related U.S. Application Data

(63) Continuation of application No. PCT/KR2022/004866, filed on Apr. 5, 2022.

(30) Foreign Application Priority Data

Dec. 8, 2021 (KR) .......................... 10-2021-0174414

(51) Int. Cl.
| | | |
|---|---|---|
| *G10L 15/00* | (2013.01) | |
| *A61B 5/00* | (2006.01) | |
| *G06F 40/279* | (2020.01) | |
| *G10L 15/22* | (2006.01) | |
| *G10L 25/66* | (2013.01) | |

(Continued)

(52) U.S. Cl.
CPC .......... *A61B 5/4088* (2013.01); *A61B 5/0022* (2013.01); *A61B 5/4803* (2013.01); *G06F 40/279* (2020.01); *G10L 15/187* (2013.01); *G10L 15/22* (2013.01); *G10L 15/30* (2013.01);
(Continued)

(58) Field of Classification Search
CPC ...... A61B 5/4088; A61B 5/4803; G10L 15/00
See application file for complete search history.

(56) References Cited

U.S. PATENT DOCUMENTS

| | | | |
|---|---|---|---|
| 2017/0105666 A1* | 4/2017 | Lee .......................... | G09B 7/06 |
| 2020/0365275 A1* | 11/2020 | Barnett ................ | A61B 5/4088 |
| 2021/0177340 A1* | 6/2021 | Sumi ...................... | A61B 10/00 |

FOREIGN PATENT DOCUMENTS

| | | |
|---|---|---|
| JP | 2020-522028 A | 7/2020 |
| KR | 10-2014-0023458 A | 2/2014 |

(Continued)

OTHER PUBLICATIONS

An Office Action mailed by Korean Intellectual Property Office dated Mar. 25, 2022, which corresponds to Korean Patent Application No. 10-2021-0174414; with English language translation.

*Primary Examiner* — Daniel Abebe
(74) *Attorney, Agent, or Firm* — Studebaker & Brackett PC

(57) ABSTRACT

The present disclosure relates to a method and a server capable of performing a dementia test without the need for a dementia test subject to personally visit a test center and capable of automatically performing a dementia test by an artificial intelligence, not an individual. According to an embodiment of the present disclosure, a dementia test may be performed without the need for a dementia test subject to personally visit a test center, thereby improving the effectiveness of a dementia test by filtering patients who need to visit the test center and proceed with a follow-up test, and a dementia test may be automatically performed by an artificial intelligence, not an individual, thereby saving the time required for the dementia test and costs such as labor cost for the test.

15 Claims, 7 Drawing Sheets

(51) Int. Cl.
*G10L 15/30* (2013.01)
*H04M 3/42* (2006.01)
*G10L 15/187* (2013.01)

(52) U.S. Cl.
CPC ......... *G10L 25/66* (2013.01); *H04M 3/42221* (2013.01)

(56) References Cited

FOREIGN PATENT DOCUMENTS

| | | |
|---|---|---|
| KR | 10-2019-0081626 A | 7/2019 |
| KR | 10-2020-0143940 A | 12/2020 |
| KR | 10-2021-0015020 A | 2/2021 |
| KR | 10-2237539 B1 | 4/2021 |
| KR | 10-2314213 B1 | 10/2021 |

\* cited by examiner

METHOD AND SERVER FOR DEMENTIA TEST BASED ON VOICE QUESTION AND ANSWER USING ARTIFICIAL INTELLIGENCE CALL

CROSS-REFERENCE TO RELATED APPLICATION

The present application is a continuation of International Patent Application No. PCT/KR2022/004866, filed on Apr. 5, 2022, which is based upon and claims the benefit of priority to Korean Patent Application No. 10-2021-0174414 filed on Dec. 8, 2021. The disclosures of the above-listed applications are hereby incorporated by reference herein in their entirety.

BACKGROUND

1. Technical Field

The present disclosure relates to a dementia test method and server based on an artificial intelligence telephone call, and more particularly, to a dementia test method and server for performing a dementia test based on question and answer using an artificial intelligence telephone call.

2. Description of Related Art

Alzheimer's disease (AD) is a brain disease accompanying aging, and is a disease resulting from brain abnormalities causing gradual deterioration of memory. In addition, AD may lead to dementia, which causes a continuous and overall decline in cognitive function to the extent that it causes difficulties in daily life. Here, cognitive function refers to various intellectual abilities such as memory, language ability, temporal and spatial awareness abilities, in addition to the ability to judge actions which should be taken, as well as capacity for abstract thought. Here, respective cognitive functions are closely related to specific parts of the brain.

Mild cognitive impairment (MCI) refers to a state in which an individual's memory and cognitive function are deteriorated compared to other individuals of the same age group, but where the individual's condition has not progressed to dementia. MCI may, however, develop into AD, and thus MCI an important symptom for the early detection of AD such that preemptive action may be taken to ameliorate the effects of AD.

A dementia (or MCI) test is generally performed in the order of a screening test, a diagnostic test, and a differential test. The screening test is performed at regional dementia care centers and public health centers. There may be an issue in the effectiveness and efficiency of such a test, in that it requires test subjects to personally visit regional dementia care centers and public health centers and staff members of such facilities to directly administer tests. Here, an individual with a low probability of having dementia may have to personally visit a test center, and the effectiveness of the test may thus be lowered. In addition, when an individual directly performs a test, it takes several tens of minutes for a single individual to be tested, which is a huge loss in terms of time and cost.

An artificial intelligence telephone call is an automated phone call to which artificial intelligence technology is applied, and uses technology in which artificial intelligence performs a call instead of an individual. The artificial intelligence telephone call automatically makes a phone connection to a plurality of people and performs a phone call according to a purpose, so that human labor can be saved.

SUMMARY

An aspect of the present disclosure is directed to providing a method and a server capable of performing a dementia test without the need for a dementia test subject to personally visit a test center.

In addition, an aspect of the present disclosure is directed to providing a method and a server capable of automatically performing a dementia test with artificial intelligence, rather than an individual.

The aspects of the present disclosure are not limited to those mentioned above, and other aspects not mentioned herein will be clearly understood by those skilled in the art from the following description.

A dementia test method performing a dementia test based on question and answer using an artificial intelligence telephone call performed on a server according to an embodiment of the present disclosure may include: providing guidance to a user terminal to which an artificial intelligence telephone call is connected; conducting a first test, which is an initial familiarization test, in order to increase a test subject's understanding of a test progress method; conducting a second test, a main test, used to determine a presence of dementia or a dementia symptom level of the test subject; analyzing content of the first test; analyzing content of the second test; and transmitting a test result to the user terminal, wherein the conducting the first test may include: providing a first question for requesting an answer to a first topic to the user terminal for a first time period; and acquiring a first answer from the user terminal; wherein the conducting the second test may include: providing a second question for requesting an answer to a second topic, different from the first topic, to the user terminal for a second time period, longer than the first time period; and acquiring a second answer from the user terminal; wherein the analyzing the content of the first test may include: calculating an understanding value, which is a value numerically quantifying a degree of the test subject's understanding of the test progress method based on the first answer; and when the understanding value is lower than a preset value, determining that the test subject does not understand the test progress method, and guiding the test progress method without conducting the second test or scheduling a test thereafter; and wherein the analyzing the content of the second test may include: converting the second answer into text data; extracting at least one word corresponding to the second topic from the text data; calculating a language fluency value based on at least one word corresponding to the extracted second topic; comparing and analyzing the language fluency value with a preset reference value; and when the language fluency value is lower than the preset reference value, determining that the test subject is a subject for a follow-up test.

In addition, the present disclosure may include a computer-readable recording medium in which a computer program for executing the aforementioned dementia test method based on an artificial intelligence telephone call is stored in combination with a computer, which is hardware.

In addition, a dementia test server performing a dementia test based on question and answer using an artificial intelligence telephone call according to an embodiment of the present disclosure may include: a communication unit communicating with a user terminal to provide an artificial intelligence telephone call, transmitting a question and test result to the user terminal, and receiving an answer from the user terminal; a dementia test progress unit providing guidance to the user terminal, conducting a first test, which is an initial familiarization test, in order to increase a test subject's understanding of a test progress method, conducting a second test, a main test, used to determine a presence of dementia or a dementia symptom level of the test subject, wherein the first test is conducted by providing a first question for requesting an answer to a first topic to the user terminal for a first time period and acquiring a first answer from the user terminal, and the second test is conducted by providing a second question for requesting an answer to a second topic, different from the first topic, to the user terminal for a second time period, longer than the first time period, and acquiring a second answer from the user terminal; and an analysis unit analyzing content of the first test by calculating an understanding value, which is a value numerically quantifying a degree of the test subject's understanding of the test progress method based on the first answer, and when the understanding value is lower than a preset value, determining that the test subject does not understand the test progress method, and guiding the test progress method without conducting the second test or scheduling a test thereafter, and analyzing content of the second test by converting the second answer into text data, extracting at least one word corresponding to the second topic from the text data, calculating a language fluency value based on at least one word corresponding to the extracted second topic, comparing and analyzing the language fluency value with a preset reference value, and when the language fluency value is lower than the preset reference value, determining that the test subject is a subject for a follow-up test.

DETAILED DESCRIPTION

Figure 1:
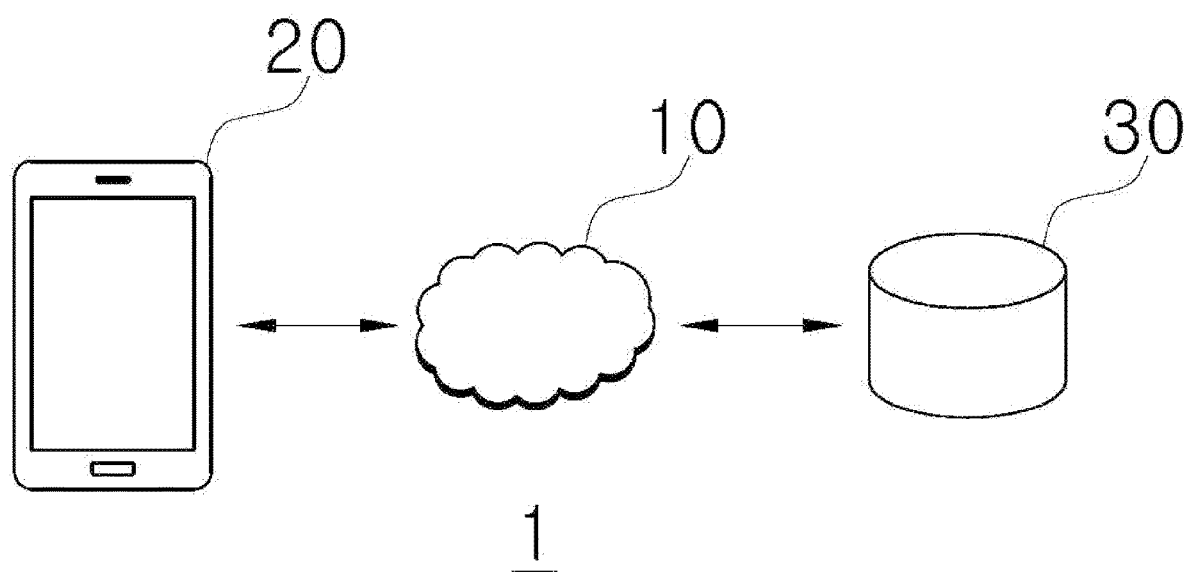
FIG. 1 is a conceptual view schematically illustrating a dementia test system according to an embodiment of the present disclosure.

The advantages and features of the present disclosure and methods of achieving them will be apparent from the embodiments that will be described in detail with reference to the accompanying drawings. It should be noted, however, that the present disclosure is not limited to the following embodiments, and may be implemented in various different forms. Rather the embodiments are provided so that this disclosure will be thorough and complete and will fully convey the scope of the present disclosure to those skilled in the technical field to which the present disclosure pertains. It is to be noted that the scope of the present disclosure is defined only by the category of the claims.

Terms used in the specification are used to describe embodiments of the present disclosure and are not intended to limit the scope of the present disclosure. In the specification, the terms in singular form may include plural forms unless otherwise specified. The expressions "comprise" and/or "comprising" used herein indicate the existence of one or more other elements other than stated elements but do not exclude presence of additional elements. Like reference denotations refer to like elements throughout the specification. As used herein, the term "and/or" includes each and all combinations of one or more of the mentioned components. It will be understood that, although the terms "first", "second", etc., may be used herein to describe various components, these components should not be limited by these terms. These terms are only used to distinguish one component from another component. Accordingly, a first component mentioned below could be termed a second component without departing from the technical ideas of the present disclosure.

As used herein, the term "artificial intelligence telephone call" refers to a phone call to which artificial intelligence technology is applied, and refers to a technology in which artificial intelligence performs a call instead of an individual.

As used herein, the term "question" may be in the form of at least one or a combination of two or more of text, image, and voice indicating a question. In the following description, it has been described that the form of the question is voice, but the present disclosure is not limited thereto.

In addition, as used herein, the term "answer" may be in the form of at least one or a combination of two or more of text, image, and voice indicating an answer. In the following description, it has been described that the form of the answer is voice, but the present disclosure is not limited thereto.

As used herein, the term "language fluency value" refers to a value numerically quantifying relevant abilities (semantic memory, executive function, working memory, etc.) to determine a presence and/or progression of dementia.

As used herein, the term "understanding value" refers to a value numerically quantifying a degree of test subject's understanding of a test progress method.

Unless otherwise defined, all terms (including technical and scientific terms) used herein have the same meaning as commonly understood by those skilled in the technical field to which the present disclosure pertains. It will be further understood that terms, such as those defined in commonly used dictionaries, should not be interpreted in an idealized or overly formal sense unless expressly so defined herein.

Hereinafter, embodiments of the present disclosure will be described in detail with reference to the accompanying drawings.

FIG. 1 is a conceptual view schematically illustrating a dementia test system according to an embodiment of the present disclosure.

As illustrated in FIG. 1, a dementia test system 1 according to an embodiment of the present disclosure may include a dementia test server 10, a user terminal 20, and an institution server 30.

The dementia test server 10 is a server performing a dementia test using an artificial intelligence telephone call. Herein, the term "artificial intelligence telephone call" refers to a phone call to which artificial intelligence technology is applied, and refers to a technology in which artificial intelligence performs a call instead of an individual. As a specific example, the artificial intelligence telephone call may provide a pre-stored voice configured of an artificial intelligence voice and/or a voice recorded by an individual to a terminal to which the artificial intelligence telephone call is connected. For example, the pre-stored voice may include a guide remark, a question voice, a closing remark, and the like.

A user may participate in the dementia test by interacting with the voice provided by an artificial intelligence telephone call and giving an answer in response thereto. In an embodiment, when it is determined that the interaction with the user based on the artificial intelligence telephone call is not smooth, it is also possible to stop providing the pre-stored voice and directly intervene to communicate with a receiver of the user terminal 20.

The dementia test server 10 may communicate with the user terminal 20. The dementia test server 10 sends an artificial intelligence telephone call to the user terminal 20 of a test subject to perform a dementia test based on voice question and answer. The dementia test server 10 determines whether a user of the user terminal 20 corresponds to a follow-up test subject by analyzing a dementia test result using the answer voice acquired from the user terminal 20 as test content during the test. This process is automatically performed by the dementia test server 10 without direct intervention of an individual (for example, a tester, an administrator, etc.), thereby dramatically saving time and costs required for the dementia test. In addition, it is possible to improve the effectiveness of a follow-up test by filtering and determining in advance whether a visiting test is necessary through a phone call before the test subject visits a test institution and participates in the test.

The dementia test server 10 determines whether a follow-up test is necessary by evaluating the language fluency of the test subject through voice question and answer based on an artificial intelligence telephone call. Specifically, the dementia test server 10 conducts a dementia test based on voice question and answer, analyzes the test subject's answer voice acquired therefrom, and calculates a language fluency value numerically quantifying the language fluency. The dementia test server 10 compares and analyzes the calculated language fluency value with a preset value to determine whether a follow-up test is necessary. For example, when the language fluency value is lower than a preset value, the corresponding user may be determined as a subject for a follow-up test, and when the language fluency value is equal to or greater than the preset value, the corresponding user may be determined as a non-subject for the follow-up test.

In an embodiment, the dementia test performed by the dementia test server 10 may be a test for screening a subject who needs to visit a test institution to conduct a screening test before conducting a three-stage test configured of a screening test, a diagnostic test, and a differential test. In this connection, a follow-up test may correspond to a screening test among the three-stage test. In another embodiment, the dementia test performed by the dementia test server 10 may correspond to a screening test among a three-stage test configured of a screening test, a diagnostic test, and a differential test, and the follow-up test may correspond to a diagnostic test among the three-stage test.

In an embodiment, as illustrated in FIG. 1, the dementia test server 10 may communicate with the institution server 30. In this connection, the dementia test server 10 may communicate with the institution server 30 to acquire test subject database from the institution server 30, and send an artificial intelligence telephone call to people included in the test subject database to conduct a dementia test. In addition, the dementia test server 10 may analyze test content based on auxiliary information included in the test subject database acquired from the institution server 30. In addition, the dementia test server 10 may autonomously store and manage a test result or transmit the test result to the institution server 30.

The subject database stored in the institution server 30 may be elderly people with a high probability of having a dementia, but is not limited thereto. In addition, the test subject database held by the institution server 30 may be grouped based on at least one of gender, age, education level, and a number of people living together.

In another embodiment, unlike illustrated in FIG. 1, it is also possible that the institution server 30 is omitted. In this connection, the dementia test server 10 may collect auxiliary information by providing a question and answer for collecting auxiliary information before the test is conducted in the user terminal 20 connected to an artificial intelligence telephone call. In addition, the test content may be analyzed based on the collected auxiliary information. The auxiliary information may include at least one of gender, age, education level, and a number of people living together, but is not limited thereto.

The user terminal 20 may be a mobile device possessed by a test subject. For example, the user terminal 20 may include all kinds of handheld-based wireless communication devices such as Personal Communication System (PCS), Global System for Mobile communications (GSM), Personal Digital Cellular (PDC), Personal Handyphone System (PHS), Personal Digital Assistant (PDA), International Mobile Telecommunication (IMT)-2000, Code Division Multiple Access (CDMA)-2000, W-Code Division Multiple Access (W-CDMA), Wireless Broadband Internet (WiBro), terminals, smart phones, and the like, and wearable devices such as watches, rings, bracelets, anklets, necklaces, glasses, contact lenses, or head-mounted-devices (HMDs) and AI speakers, and the like. However, the user terminal 20 is not limited to the above-described example, and may include any device having portability and communication properties.

The user terminal 20 may include a communication unit. The user terminal 20 may make a phone connection to the dementia test server 10 through the communication unit, or may transmit/receive data to and from the dementia test server 10. The communication unit may include at least one of a short-range communication module, a wired communication module, and a wireless communication module.

The user terminal 20 may include a sound acquisition unit. The sound acquisition unit may acquire a voice of an individual, such as a test subject, a third party, or various sounds existing around the user terminal 20. In an embodiment, the sound acquisition unit may be a microphone that functions as a sensor for receiving various sounds around the user terminal 20. The sound acquisition unit of the user terminal 20 may receive a sound signal generated around the user terminal 20 while an artificial intelligence telephone call is connected and serve as a converter to convert the sound signal into an electric signal.

In an embodiment, the user terminal 20 may further include a camera unit for performing imaging and a display unit for displaying an image. In this connection, the artificial intelligence telephone call provided by the dementia test server 10 may be implemented as a video call as well as a general voice call.

The institution server 30 is a server operated by a test institution. As used herein, the term "test institution" may be an institution performing a dementia test, such as a dementia care center, a public health center, and the like, but is not limited thereto.

The institution server 30 may include a communication unit to communicate with the dementia test server 20. The institution server 30 may receive data such as a test result from the dementia test server 20, or transmit data such as a test subject database to the dementia test server 20.

The institution server 30 may store and manage a test subject database. In an embodiment, the institution server 30 may intensively store and manage a database of people of a specific age group (for example, 50 years or older) in a nearby area. This test subject database may be transmitted to the dementia test server 20, and the dementia test server 20 may send an artificial intelligence telephone call to the people included in the test subject database to conduct a dementia test. In another embodiment, the dementia test server 20 may be given a receivable phone number and receive a phone call made to the corresponding phone number. In this connection, when a test subject makes a phone call to the phone number provided by the dementia test server 20, the dementia test server 20 may receive the corresponding phone call and conduct a dementia test based on an artificial intelligence telephone call.

The institution server 30 may receive the test result from the dementia test server 20 and update the existing test subject database. The test institution 30 may continuously update, store and manage the test results and test histories of people included in the test subject database. In an embodiment, the institution server 30 may exclude those who have a test history within a preset period in the test subject database from the test subject until the corresponding period passes. Thus, the dementia test server 10 may selectively send artificial intelligence telephone calls only to test subjects who actually need tests, excluding those who have a recent test history, thereby preventing meaningless artificial intelligence telephone call transmissions.

In an embodiment, the institution server 30 may be omitted. In this connection, the function of the aforementioned institution server 30 may be performed by the dementia test server 20. In other words, the dementia test server 20 may manage a test subject database, and may send artificial intelligence telephone calls only to people who do not have a test history within a preset period. In another embodiment, it is also possible that the dementia test server 20 and the institution server 30 are operated as an integrated server rather than as an independent server.

Figure 2:
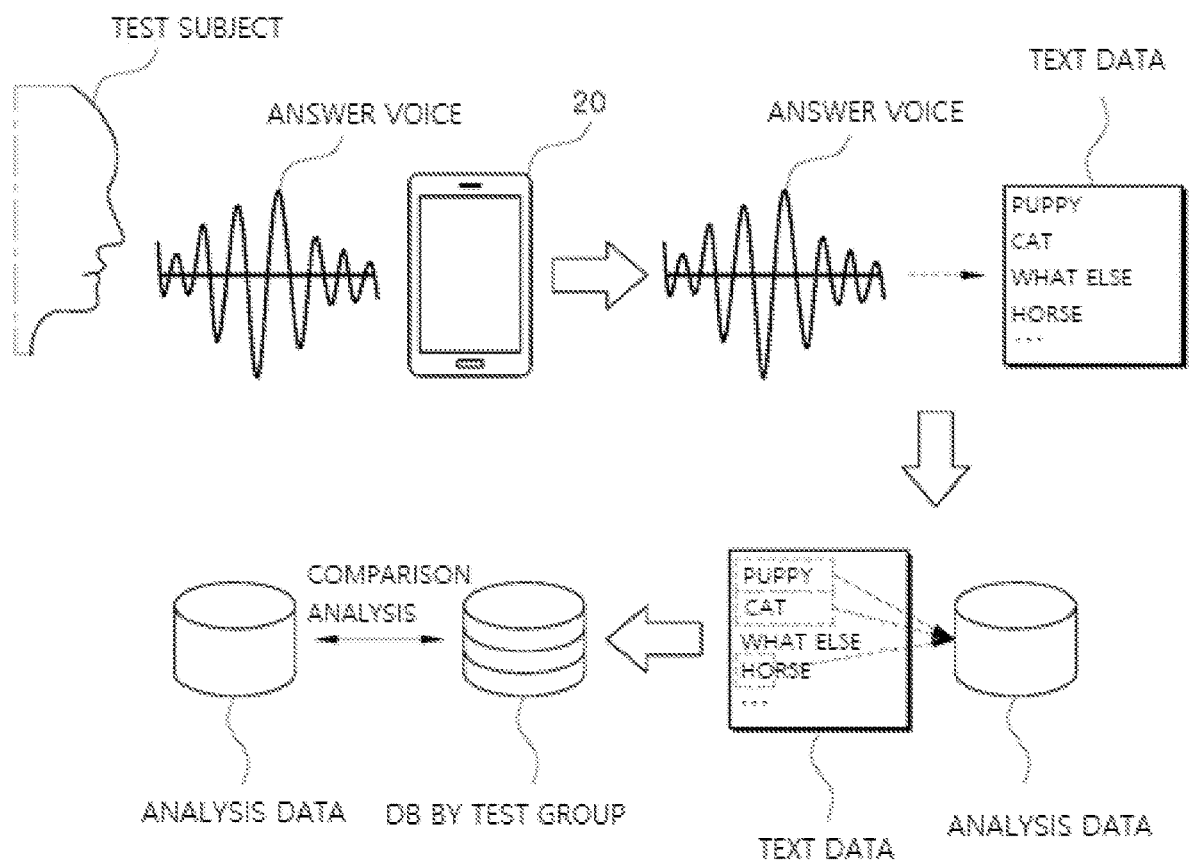
FIG. 2 is an exemplary view schematically illustrating a process in which a dementia test based on an artificial intelligence telephone call is conducted according to an embodiment of the present disclosure.

FIG. 2 is an exemplary view schematically illustrating a process in which a dementia test based on an artificial intelligence telephone call is conducted according to an embodiment of the present disclosure.

As illustrated in FIG. 2, the dementia test based on an artificial intelligence telephone call according to an embodiment of the present disclosure may be performed through the processes of performing a question and answer for the dementia test on the user terminal 20 to which the artificial intelligence telephone call is connected, and converting the answer voice acquired from the user terminal 20 into text data and then analyzing the same.

First, the dementia test server 10 (see FIG. 1) sends an artificial intelligence telephone call to the user terminal 20 of a test subject. The dementia test server 10 may perform a dementia test based on question and answer with the user terminal 20 to which the artificial intelligence telephone call is connected, and the answer voice of the test subject during the test may be acquired through the user terminal 20 and then transmitted to the dementia test server 10.

The dementia test server 10 may convert the answer voice of a test subject received from the user terminal 20 to character data. The answer voice of the test subject may include not only the words uttered by the test subject that intend to answer to questions provided during a dementia test, but also the words that do not intend to answer to questions such as exclamatory words and mumbling. For example, referring to the character data into which the answer voice illustrated in FIG. 2 is converted, the answer voice may include "puppy," "cat," "what else," "horse," and the like. Herein, "puppy", "cat" and "horse" correspond to the words that the test subject utters for the purpose of answering to questions provided during a dementia test, and thus may be a significantly utilized for analyzing test content. On the other hand, "what else" corresponds to mumbling that is not intended to answer questions, so it is not helpful in analyzing test content. The dementia test server 10 can improve the efficiency and accuracy of the test by extracting only words that may be significantly utilized for analyzing test content among character data and performing an analysis.

The dementia test server 10 calculates a numerical value capable of determining a presence of dementia or a dementia symptom level of a test subject based on the extracted words. The dementia test server 10 compares and analyzes the numerical value with the pre-stored database for each test group to determine whether the test subject needs to visit a test institution to conduct a follow-up test.

Figure 3:
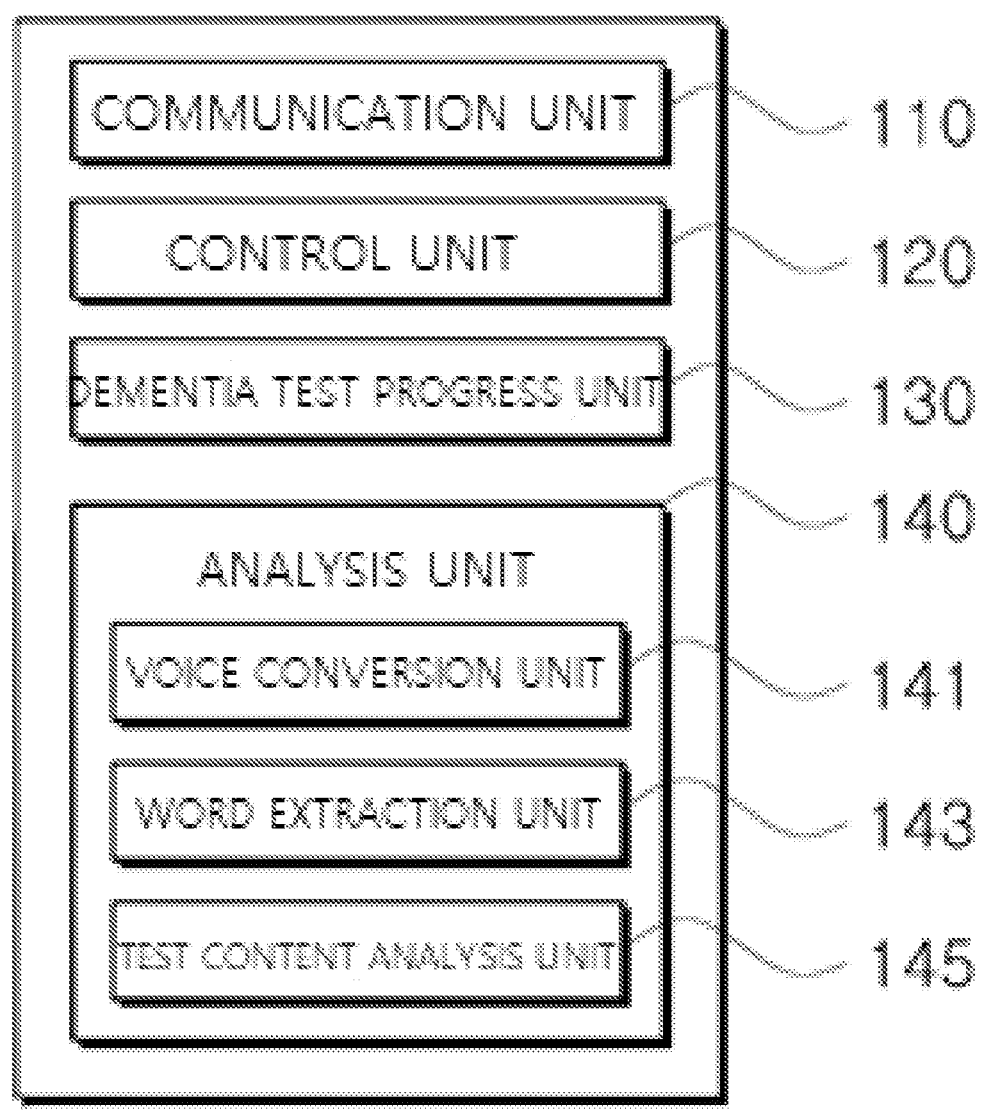
FIG. 3 is a block view schematically illustrating a portion of a dementia test server according to an embodiment of the present disclosure.

FIG. 3 is a block view schematically illustrating a portion of a dementia test server according to an embodiment of the present disclosure.

As illustrated in FIG. 3, the dementia test server 10 according to an embodiment of the present disclosure may include a communication unit 110, a control unit 120, a dementia test progress unit 130, and an analysis unit 140.

Some components included in the dementia test server 10 may be deleted or implemented integrally with other components as needed. In addition, other components not illustrated in FIG. 3 may be added. In other words, the types of components included in the dementia test server 10 and the mutual positions of the components may be variously modified as needed.

The communication unit 110 serves to communicate with the user terminal 20 (see FIG. 1) and/or the institution server 30 (see FIG. 1). The communication unit 110 may include at least one of a short-range communication module, a wired communication module, and a wireless communication module.

For example, the short-range communication module may include various short-range communication modules for transmitting and receiving signals within a short range over a wireless communication network, such as a Bluetooth module, an infrared communication module, a radio frequency identification (RFID) communication module, a wireless local access network (WLAN) communication module, a near field communication (NFC) module, a Zigbee communication module, etc.

The wired communication module may include not only one of the various wired communication modules, such as a local area network (LAN) module, a wide area network (WAN) module, or a value added network (VAN) module, but also one of various cable communication modules, such as a universal serial bus (USB), a high definition multimedia interface (HDMI), a digital visual interface (DVI), recommended standard (RS) 232, a power cable, or a plain old telephone service (POTS).

The wireless communication module may include a wireless fidelity (Wi-Fi) module, a wireless broadband (WiBro) module, and any wireless communication module for supporting various wireless communication schemes, such as a global system for a mobile communication (GSM) module, a code division multiple access (CDMA) module, a wideband code division multiple access (WCDMA) module, a universal mobile telecommunications system (UMTS), a time division multiple access (TDMA) module, a long-term evolution (LTE) module, and 5G.

The control unit 120 may be implemented using a memory (not shown) configured to store data for algorithms to control operation of components of the user terminal 20 or programs constructed from algorithms, and a processor (not shown) configured to execute the operation by using data stored in the memory. In this case, the memory and the processor may be implemented using separate chips or integrated into a single chip.

The dementia test server 10 may further include a storage unit (not shown) for storing and managing test subject database, test content, test content analysis result, test history, and the like. The storage unit may be implemented using at least one of a non-volatile memory device including cache memory, Read Only Memory (ROM), Programmable ROM (PROM), Erasable Programmable ROM (EPROM), Electrically Erasable Programmable ROM (EEPROM), and flash memory, a volatile memory device including Random Access Memory (RAM), or a storage medium including Hard Disk Drive (HDD) and CD-ROM, without being limited thereto. The storage unit may be implemented as a separate chip from the processor described above regarding the control unit 120 or a single chip.

The dementia test progress unit 130 serves to conduct a dementia test on a test subject of the user terminal 10 to which an artificial intelligence telephone call is connected. The dementia test performed by the dementia test progress unit 130 may be conducted based on a voice question and answer. For example, the dementia test progress unit 130 may conduct the dementia test by providing a question for the test to the user terminal 20 (see FIG. 1) and acquiring the test subject's answer voice from the user terminal 20. Specifically, the dementia test progress unit 130 may provide a specific topic (or criteria, category, etc.) to the test subject, and provide a question voice requesting to answer as many words as possible corresponding to the topic for a preset time period. The dementia test progress unit 130 may acquire an answer voice answered by a user in response to the question voice.

In an embodiment, the dementia test performed by the dementia test progress unit 130 may include a first test and a second test that are sequentially conducted. The "first test" may be a practice test preceded in order to increase the understanding of the test before conducting the second test. In addition, the "second test" may be a main test that is actually used to determine a presence of dementia or a dementia symptom level of a test subject.

Details of the dementia test performed by the dementia test progress unit 130 will be described later with reference to FIGS. 4 to 6.

The dementia test progress unit 130 performs a dementia test, and the test subject's answer voice acquired from the user terminal 20 (see FIG. 1) may be transmitted to the analysis unit 140.

The analysis unit 140 analyzes test content based on the answer voice received from the dementia test progress unit 130. In an embodiment, as illustrated in FIG. 3, the analysis unit 140 may include a voice conversion unit 141, a word extraction unit 143, and a test content analysis unit 145.

The voice conversion unit 141 may serve to convert the answer voice received from the dementia test progress unit 130 into text data. Speech-to-text (STT) conversion technology may be applied to the voice conversion unit 141, and there is no limitation on the type of STT conversion technology.

In an embodiment, the voice conversion unit 141 may divide the answer voice into segments, convert the answer voice into a text for each segment, and then switch the answer voice into text data by integrating the converted text segments. To this end, the voice conversion unit 141 may include a voice separation unit (not shown), a text conversion unit (not shown), and a text integration unit (not shown), but is not limited thereto.

The word extraction unit 143 serves to extract at least one word from the text data acquired by the voice conversion unit 141 converting the answer voice of a test subject.

The word extraction unit 143 may extract at least one word related to test content from the entire text data in which the answer voice acquired during a dementia test is converted. For example, when the dementia test performed by the dementia test progress unit 130 is conducted in such a way that as many words as possible corresponding to a specific topic are answered for a preset time period, the word extraction unit 143 may extract words related to the test content from the text data in which the answer voice of a test subject is converted. Specifically, the word extraction unit 143 may extract only the words corresponding to the answer to the given topic in the test from the answer voice of the test subject.

The test content analysis unit 145 serves to analyze test content based on at least one word extracted by the word extraction unit 143.

The test content analysis unit 145 may calculate a language fluency value based on at least one word extracted by the word extraction unit 143, and analyze test content in a way that compares and analyzes the language fluency value with a preset reference value.

Herein, the term "language fluency value" refers to a value numerically quantifying relevant abilities (semantic memory, executive function, working memory, etc.) to determine a presence and/or progression of dementia. The language fluency value may be calculated in a way of applying and then scoring an adjusted score criterion to at least one of a total number of words, a number of words in a first half, a number of words in a second half, a number of letters per word, a number of category changes, a number of words by category, and a number of repeated words extracted from the test subject's answer. The type, number, and weight of variables used to calculate the language fluency value may be variously modified.

As a specific example, the test content analysis unit 145 may calculate the language fluency value through the following equation.

$$LFV = a1*A + a2*B + a3*C + a4*D + a5*E + a6*F + a7*G \quad \text{[Equation 1]}$$

LFV: Language fluency value
A: Total number of words
B: Number of words in a first half
C: Number of words in a second half
D: Average number of characters per word
E: Number of category changes F: Average number of words by category G: Number of repeated words a1~a7: Weight variable (a1+a2+a3+a4+a5+a6+a7=1 is satisfied, a1~a7 are each a constant between 0 and 1)

In an embodiment, the language fluency value may be calculated by reflecting not only the answer content of a test subject but also auxiliary information. As used herein, the term "auxiliary information" refers to basic information such as personal information about the test subject, for example, gender (male, female), age (teens, 20s, 30s, 40s, 50s, 60s, 70s, 80s, 90s, etc.), education level (for example, elementary school graduation, middle school graduation, high school graduation, bachelor's degree, master's degree, doctorate, etc.), number of people living together (1 person, 2 people, 3 people, 4 people, etc.). The test content analysis unit 145 may differentially apply the type, number, weight, etc. of variables used to calculate the language fluency value based on auxiliary information such as age, gender, education level, number of people living together, etc. to calculate the language fluency value more accurately.

The test content analysis unit 145 may compare and analyze the calculated language fluency value with a preset value to determine whether a test subject has dementia or a progression level. As used herein, the term "preset value" may be a preset comparison reference value for determining the level of the language fluency value calculated as a result of a test. The preset values may be set differently for each group by grouping test subjects according to gender, age, education level, number of people living together, and the like. For example, the reference value of the language fluency value may be preset according to gender (male, female), age (teens, 20s, 30s, 40s, 50s, 60s, 70s, 80s, 90s, etc.), educational level (elementary school graduation, middle school graduation, high school graduation, bachelor's degree, master's degree, doctorate, etc.), and the number of people living together (1 person, 2 people, 3 people, 4 people, etc.). The reference value of the language fluency value may be set based on the test results of test finishers belonging to the corresponding group, and may be continuously updated and managed based on the information of additional test finishers.

Figure 4:
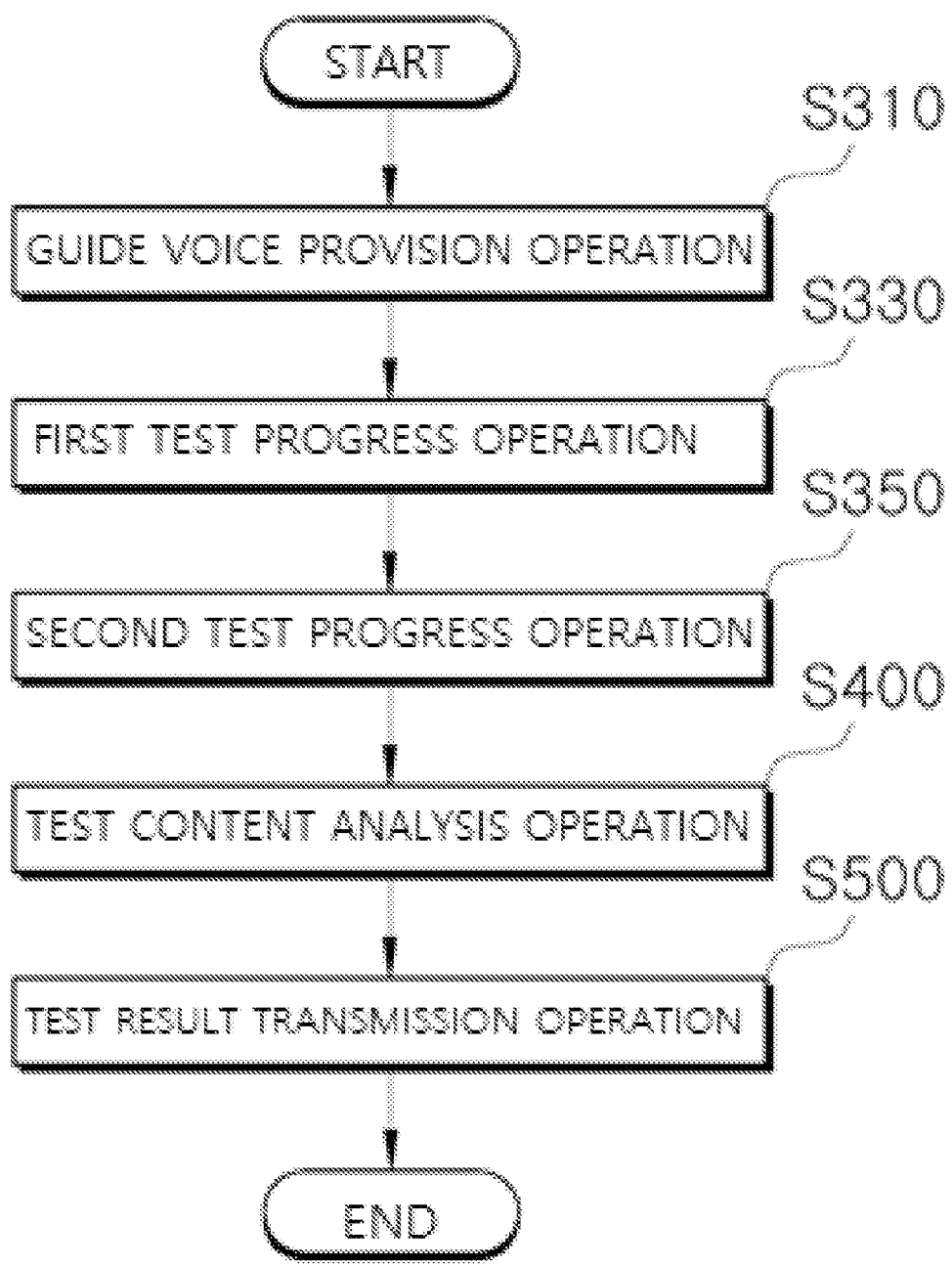
FIG. 4 is a flowchart schematically illustrating a portion of a dementia test method according to an embodiment of the present disclosure.

FIG. 4 is a flowchart schematically illustrating a portion of a dementia test method according to an embodiment of the present disclosure. FIG. 5 is a flowchart schematically illustrating a portion of a dementia test method according to an embodiment of the present disclosure.

Figure 5:
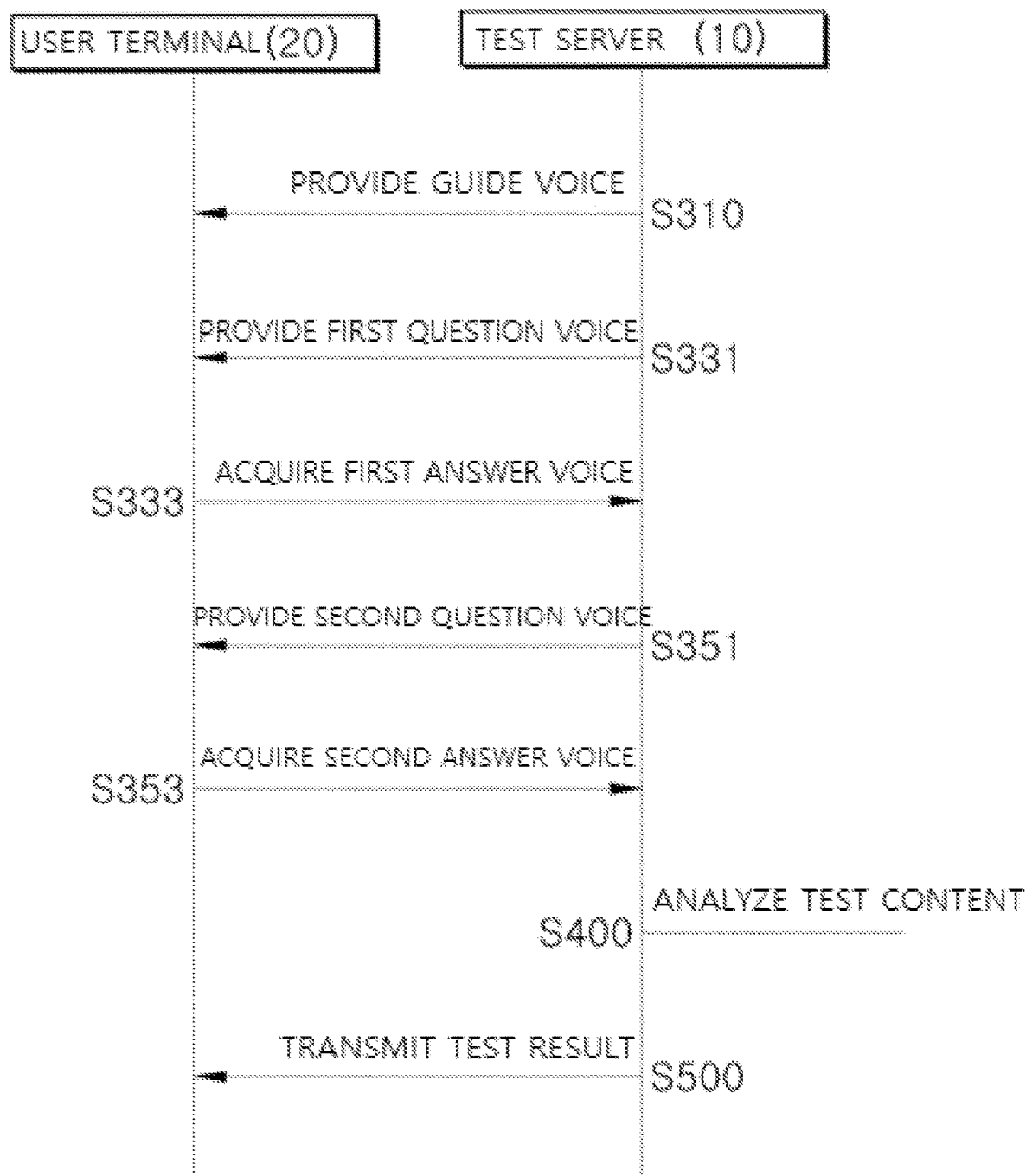
FIG. 5 is a flowchart schematically illustrating a portion of a dementia test method according to an embodiment of the present disclosure.

As illustrated in FIGS. 4 and 5, the dementia test method according to an embodiment of the present disclosure may include a guide voice provision operation (S310), a first test progress operation (S330), a second test progress operation (S350), a test content analysis operation (S400), and a test result transmission operation (S500).

The guide voice provision operation (S310) is an operation of providing a guide voice to the user terminal 20 (see FIG. 1) to which an artificial intelligence telephone call sent by the test server 10 is connected.

The guide voice may include content for preventing a test subject who has received an artificial intelligence telephone call from disconnecting the phone call without conducting a test by recognizing the phone call as a spam call. In an embodiment, the guide voice may include test subject (recipient) information, test institution information, test solution (program) information, recommender information, contact information acquisition path, compensation information provided upon completion of the test, and the like in the first half. In this connection, the test subject (recipient) information is inserted based on the aforementioned test subject database, so that the guide voice may be customized for each test subject. Thus, it is possible to improve the test participation rate of test subjects who have received the artificial intelligence telephone call.

After the voice guide is provided, a dementia test may be conducted, and the dementia test may be configured of a first test and a second test that are sequentially conducted.

The first test progress operation (S330) is an operation of conducting a first test, which is a practice test, and improving a test subject's understanding of a test progress method (a recipient of the user terminal 20).

Referring to FIG. 5, the first test progress operation (S330) may include an operation of providing, by the test server 10, a first question voice to the user terminal 20 (S331), and an operation of acquiring, by the test sever 10, a first answer voice from the user terminal 20 (S333).

The first question voice may include a voice requesting an answer to a first topic for a first time period, and the first answer voice may include a voice answered by a test subject in response to the first question voice.

A test subject may participate in a first test by giving an answer in response to the first question voice. The test subject's first answer voice may be acquired through the sound acquisition unit of the user terminal 20, and may be transmitted to the dementia test server 10 through the communication unit of the user terminal 20.

In an embodiment, the first answer voice acquired through the first test may be used as data for determining whether a test subject properly understands a test progress method. In other words, the dementia test method based on an artificial intelligence telephone call according to an embodiment of the present disclosure may further include an operation of determining a degree of the test subject's understanding of the test progress method based on the first answer voice.

For example, the dementia test server 10 may calculate an understanding value of a test subject of a test progress method and determine whether to conduct a test based thereon. As used herein, the term "understanding value" refers to a value numerically quantifying a degree of test subject's understanding of a test progress method. As a specific example, the dementia test server 10 may calculate an understanding value based on the ratio of the word voice answered in response to the first question voice among the first answer voice and other voices, and when the calculated understanding value is lower than a preset value, a second test may not be conducted. As another specific example, the dementia test server 10 may calculate an understanding value based on the number of words that the test subject answers to the first topic presented in a first test, and when the calculated understanding value is lower than a preset value, the second test may not be conducted. When it is determined that the test subject does not properly understand the test progress method and the second test is not conducted, the dementia test server 10 may provide a voice guiding the test process method or schedule the test thereafter, but is not limited thereto.

In this connection, the dementia test server 10 may provide a voice guiding a test progress method or schedule a test thereafter, but is not limited thereto.

In another embodiment, the operation of acquiring the first answer voice from the user terminal 20 may be omitted from the first test progress operation (S330). Since a first test is only a test to increase the understanding of a test progress method and is not used as data for determining the language fluency of a test subject, acquisition of an answer voice to the first test may be omitted. Thus, it is possible to reduce the total amount of data transmitted and received during a test process.

The second test progress operation (S350) is an operation of conducting a second test, a main test, and securing voice data utilized to determine a presence of dementia and a dementia symptom level.

Referring to FIG. 5, the second test progress operation (S350) may include an operation of providing, by the test server 10, a second question voice to the user terminal 20 (S351), and an operation of acquiring, by the test sever 10, a second answer voice from the user terminal 20 (S353).

The second question voice may include a voice requesting an answer to a second topic for a second time period, and the second answer voice may include a voice answered by a test subject in response to the second question voice.

A test subject may participate in a second test by giving an answer in response to the second question voice. The test subject's second answer voice may be acquired through the sound acquisition unit of the user terminal 20, and may be transmitted to the dementia test server 10 through the communication unit of the user terminal 20.

The test content analysis operation (S400) is an operation in which the dementia test server 10 analyzes test content based on the second answer voice acquired from the user terminal 20.

In the test content analysis operation (S400), the analysis unit 140 (see FIG. 3) of the dementia test server 10 may convert the second answer voice received from the user terminal 20 into text data, and analyze the test content by calculating the language fluency value based on the converted text data. Specifically, the test content analysis operation (S400) may include: an operation of converting a second answer voice received from the user terminal 20 into text data; an operation of extracting at least one word corresponding to a second topic of a second test from the converted text data; an operation of calculating a language fluency value based on at least one word corresponding to the extracted second topic; an operation of comparing and analyzing the language fluency value with a preset reference value; and when the language fluency value is lower than the preset reference value, determining a test subject as a subject for a follow-up test, and when the language fluency value is equal to or greater than the preset reference value, determining that the test subject is a non-subject for the follow-up test.

The operation of calculating the language fluency value may include an operation of applying and then scoring an adjusted score criterion to at least one of a total number of words, a number of words in a first half, a number of words in a second half, a number of letters per word, a number of category changes, a number of words by category, and a number of repeated words. In an embodiment, the language fluency value may be calculated using Equation 1 described above.

In addition, a preset reference value for comparing the calculated language fluency values may be set differentially for each of test groups classified based on auxiliary information including at least one of gender, age, education level, and a number of people living together. The calculated language fluency value may be compared and analyzed with a reference value set for a group to which the test subject belongs.

In an embodiment, the test content analysis operation (S400) further includes an operation of analyzing a change in speech style based on the second answer voice acquired through the current test and the existing test data of the test subject, in the case of a test subject having a test history, that is, when the user terminal 20 to which an artificial intelligence telephone call is connected has a test history. As used herein, the term "speech style" may include, but is not limited to, speech speed, pronunciation accuracy, and the like.

The analysis unit 140 (see FIG. 3) of the dementia test server 10 may analyze a speech style of the second answer voice acquired in the current test, and compare the same with the analyzed data of the speech style of the answer voice acquired in the previous test and calculate a speech style change value. The analysis unit 140 of the dementia test server 10 may determine a subject for a follow-up test when the speech style change value is equal to or greater than a specific value (a preset value). In addition, the analysis unit 140 of the dementia test server 10 may determine a subject for a follow-up test when a difference between the language fluency value calculated in the previous test and the language fluency value calculated in the current test is equal to or greater than a specific value (preset value). Thus, not only when the size of the absolute language fluency value, but also when the language fluency is relatively lowered compared to the time of the previous test, a follow-up test is performed to prevent the symptoms from rapidly worsening in advance.

In an embodiment, the test content analysis operation (S400) may further include an operation of determining a degree of understanding of a test progress method based on a first answer voice. Specifically, the dementia test server 10 may analyze a first answer voice to determine whether a test subject fully understands and answers the test progress method, or does not understand the method and gives an answer irrelevant to test content. For example, the dementia test server 10 may determine that the test subject has properly understood the test progress method if the test subject answers more than a preset number of words for the first topic presented in the first test, and if not, may determine that the test subject has not properly understood the test progress method.

Even when the language fluency value calculated by analyzing the second answer voice is less than a preset reference value, and when the understanding value of the test progress method calculated by analyzing the first answer voice is less than a specific value (preset value), the dementia test server 10 may conduct a retest after re-guiding a test method without immediately determining that the test subject is a subject for a follow-up test. Thereby, it is possible to distinguish a case in which a test subject who actually has excellent language fluency (without dementia symptoms) has received a low language fluency value due to a lack of understanding of the test progress method, thereby improving the accuracy of the test.

The test result transmission operation (S500) is an operation of transmitting a test result analyzed in the test content analysis operation (S400) to the user terminal 20.

As an embodiment, the test result may be transmitted in the form of a message, and the message may include a link for checking the test result. The method of transmitting the test result is not limited to the above-described example, and may be provided in various forms such as phone call, mail, and message. In addition, the subject receiving the test result is not limited to the test subject, and may be applied to various people around the test subject such as a housemate or guardian.

In an embodiment, the test result may include whether a test subject corresponds to a subject for a follow-up test and future symptom prediction information. As used herein, the future symptom prediction information is derived based on symptom information of people in a similar group with similar auxiliary information (for example, age, gender, education level, number of people living together) to the test subject, and may include trends in the decrease in language fluency values over time, progress results of follow-up tests, and the like.

Figure 6:
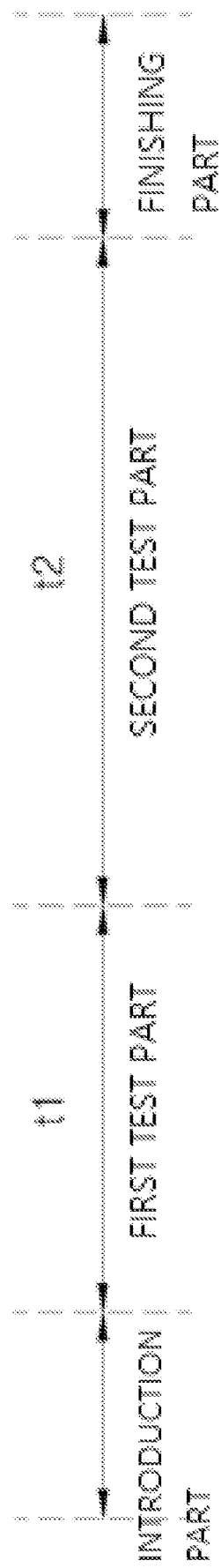
FIG. 6 is an exemplary view schematically illustrating a time-series process of a test progress operation according to an embodiment of the present disclosure.

FIG. 6 is an exemplary view schematically illustrating a time-series process of a test progress operation according to an embodiment of the present disclosure.

As illustrated in FIG. 6, the test progress operation according to an embodiment of the present disclosure may include an introduction part, a first test, a second test, and a finishing part.

The introduction part may correspond to a guide voice provision operation (S310, see FIG. 4), the first test part may correspond to the first test progress operation (S330, see FIG. 4), and the second test part may correspond to the second test progress operation (S350, see FIG. 4). In addition, the finishing part may be an operation of providing a final voice after the second test is completed. This finishing part may be omitted if necessary.

The "first test" may be a practice test preceded in order to increase the understanding of the test before conducting the second test. In addition, the "second test" may be a main test that is actually used to determine a presence of dementia symptom of a test subject.

The first test and the second test may have the same test progress method. For example, both the first test and the second test may be tests of answering as many words as possible corresponding to a given topic during a preset time period. The test subject conducts the first test, which is a practice test, to increase the understanding of the test progress method, and when conducting the second test, a main test, it is possible to escape from the variables caused by the lack of understanding of the test process method. Accordingly, the accuracy of the dementia test may be improved.

The first test and the second test performed by the dementia test progress unit 130 have the same test progress method, but the presented topic may be different. For example, the first test may request to answer as many words as possible corresponding to a first topic, and the second test may request to answer as many words as possible corresponding to a second topic. In this connection, the first topic of the first test and the second topic of the second test may be different from each other. As a specific example, the first topic of the first test may be "plants," and the second topic of the second test may be "animals," but is not limited thereto. The first topic and the second topic may be variously modified, and may include any subject that is different from each other.

Thereby, it is possible to prevent a decrease in the accuracy of the test as a test subject applies the words recalled during the first test to the second test as it is. In other words, through the first test, which is a practice test, the test subject merely increases the understanding of a test progress method, but cannot train in advance for the answer to the second test, a main test. Also in the second test, the accuracy of the test can be improved because the answer needs to be given by demonstrating memory ability and quickness.

In addition, the progress time of the first test and the progress time of the second test may be different from each other. Specifically, the first test may be conducted by requesting an answer to the first topic for a first time period, and the second test may be conducted by requesting an answer to the second topic for a second time period. In this connection, the first time period, which is the progress time of the first test, may be shorter than the second time period, which is the progress time of the second test. For example, the first time period, which is the progress time of the first test, may be 10 seconds or more and 30 seconds or less, and the second time period, which is the progress time of the second test, may be 30 seconds or more and 60 seconds or less, but is not limited thereto. It may be variously modified to satisfy that the first time period is shorter than the second time period. Thereby, it is possible to improve the efficiency and concentration of a test by preventing the overall test time from being unnecessarily long by only performing the role of improving the understanding of a test progress method, which is the purpose of the first test.

Figure 7:
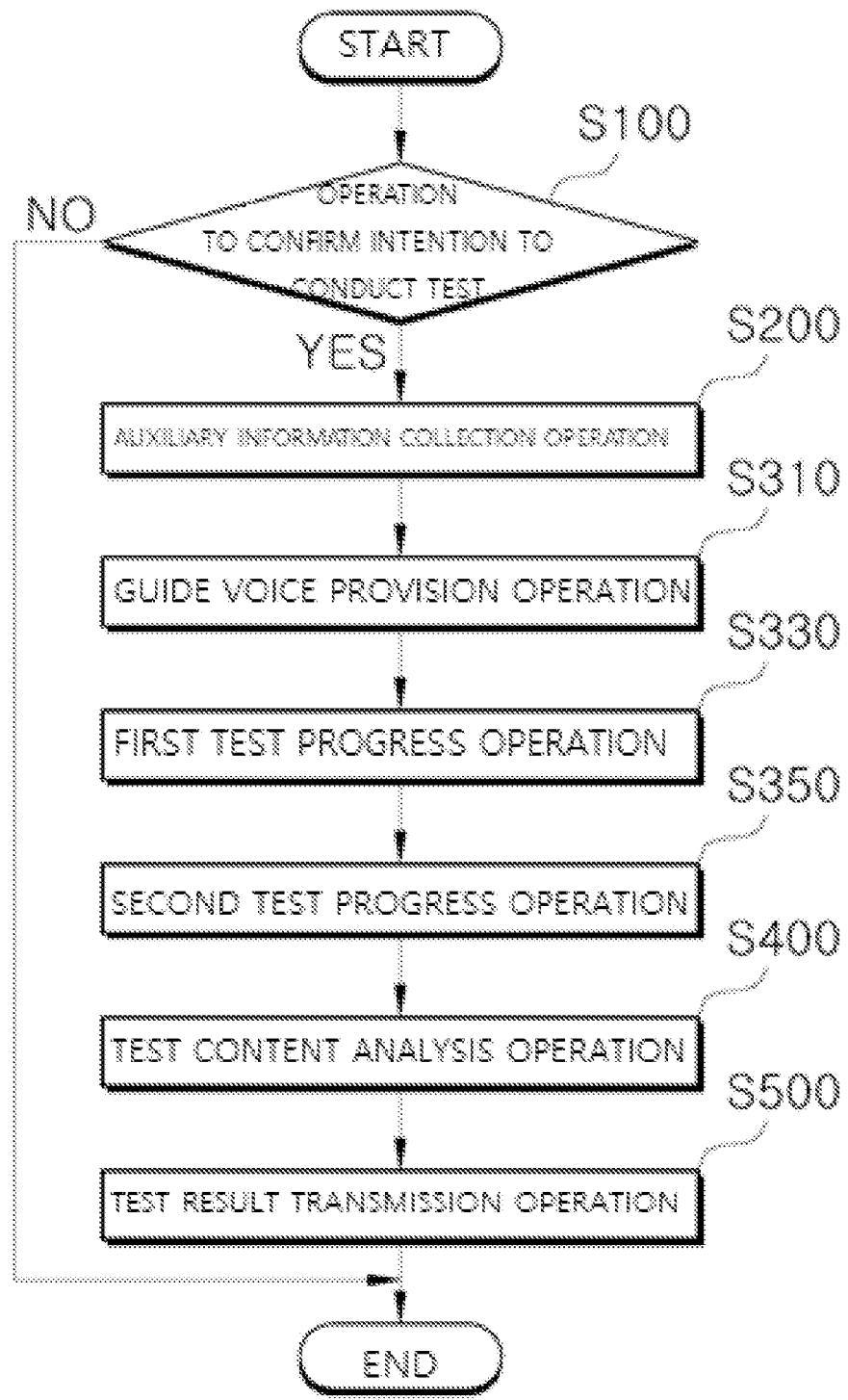
FIG. 7 is a flowchart schematically illustrating a portion of a dementia test method according to an embodiment of the present disclosure.

FIG. 7 is a flowchart schematically illustrating a portion of a dementia test method according to an embodiment of the present disclosure. Hereinafter, the same reference numerals in the drawings indicate the same components, and descriptions of the contents overlapping with the above-described contents will be omitted.

As illustrated in FIG. 7, a dementia test method based on an artificial intelligence telephone call according to an embodiment of the present disclosure may further include an operation to confirm an intention to conduct a test (S100) and an auxiliary information collection operation (S200). It is also possible to further include any one of operations S100 and S200, and omit the other one.

The operation to confirm the intention to conduct the test (S100) is an operation of confirming the intention to conduct the test before conducting a dementia examination on a test subject to which an artificial intelligence telephone call is connected. The operation to confirm the intention to conduct the test (S100) may be performed based on voice question and answer. Specifically, the operation to confirm the intention to conduct the test (S100) may include an operation of providing a voice asking a user terminal to which the artificial intelligence telephone call is connected to the intention to conduct the test, an operation of acquiring a test progress intention answer voice from the user terminal, and an operation of confirming an intention to conduct a test of the test subject based on the test progress intention answer voice.

The dementia test server 10 may conduct the aforementioned dementia test when a test progress intention answer voice is positive, and end a call or schedule a test thereafter when the test progress intention answer voice is negative. The test progress intention answer voice may be analyzed after being converted into text data by applying Speech-to-text (STT) conversion technology.

The auxiliary information collection operation (S200) is an operation of collecting auxiliary information that may be utilized for analysis of test content before conducting a test.

The auxiliary information collection operation (S200) may include an operation of providing an auxiliary information question voice asking any one of gender, age, education level, and a number of people living together to a user terminal, and acquiring an auxiliary information answer voice from the user terminal. Incompleteness of the test subject database may be supplemented by conducting the auxiliary information collection operation (S200) as described above. Meanwhile, the auxiliary information answer voice may be analyzed after being converted into text data by applying Speech-to-text (STT) conversion technology.

The auxiliary information collected through the auxiliary information collection operation (S200) may be utilized for analysis of test content. Specifically, the dementia test method based on an artificial intelligence telephone call according to an embodiment of the present disclosure may further include an operation of classifying a test group. The operation of classifying the test group may include an operation of converting an auxiliary information answer voice into text data and an operation of classifying the test group based on the text data. In other words, the dementia test server may classify the group to which the test subject belongs based on the collected auxiliary information, and apply a preset reference value for comparing the language fluency values set in the group to more accurately derive the dementia test result.

The steps of a method or algorithm described in connection with the embodiments of the present disclosure may be embodied directly in hardware, in a software module executed by hardware, or in a combination thereof. The software module may reside on a Random Access Memory (RAM), a Read Only Memory (ROM), an Erasable Programmable ROM (EPROM), an Electrically Erasable Programmable ROM (EEPROM), a Flash memory, a hard disk, a removable disk, a CD-ROM, or a computer readable recording medium in any form well known in the technical field to which the present disclosure pertains.

As set forth above, according to an embodiment of the present disclosure, a dementia test may be performed without the need for a dementia test subject to personally visit a test center, thereby improving the effectiveness of a dementia test by filtering patients who need to visit the test center and proceed with a follow-up test.

In addition, according to an embodiment of the present disclosure, a dementia test may be automatically performed with artificial intelligence, rather than an individual, thereby saving the time required for the dementia test and costs such as labor cost for the test.

The advantages of the present disclosure are not limited to those mentioned above, and other advantages not mentioned herein will be clearly understood by those skilled in the art as set forth above.

Although the embodiments of the present disclosure have been described with reference to the attached drawings, those skilled in the technical field to which the present disclosure pertains will understand that the present disclosure may be practiced in other detailed forms without departing from the technical spirit or essential features of the present disclosure. Therefore, it should be understood that the above-described embodiments are exemplary in all aspects rather than being restrictive.

The invention claimed is:

1. A dementia test method based on an artificial intelligence telephone call performing a dementia test based on question and answer using the artificial intelligence telephone call performed on a server, the method including:
    providing guidance to a user terminal to which an artificial intelligence telephone call is connected;
    conducting a first test, which is an initial familiarization test, in order to increase a test subject's understanding of a test progress method;
    conducting a second test, a main test, used to determine a presence of dementia or a dementia symptom level of the test subject;
    analyzing content of the first test;
    analyzing content of the second test; and
    transmitting a test result to the user terminal,
    wherein the conducting the first test includes:
    providing a first question for requesting an answer to a first topic to the user terminal for a first time period; and
    acquiring a first answer from the user terminal;
    wherein the conducting the second test includes:
    providing a second question for requesting an answer to a second topic, different from the first topic, to the user terminal for a second time period, longer than the first time period; and
    acquiring a second answer from the user terminal;
    wherein the analyzing the content of the first test includes:
    calculating an understanding value, which is a value numerically quantifying a degree of the test subject's understanding of the test progress method based on the first answer; and
    when the understanding value is lower than a preset value, determining that the test subject does not understand the test progress method, and guiding the test progress method without conducting the second test or scheduling a test thereafter; and
    wherein the analyzing the content of the second test includes:
    converting the second answer into text data;
    extracting at least one word corresponding to the second topic from the text data;
    calculating a language fluency value based on at least one word corresponding to the extracted second topic;
    comparing and analyzing the language fluency value with a preset reference value; and
    when the language fluency value is lower than the preset reference value, determining that the test subject is a subject for a follow-up test.

2. The dementia test method of claim 1, wherein the first time period is 10 seconds or more and 30 seconds or less, and the second time period is 30 seconds or more and 60 seconds or less.

3. The dementia test method of claim 1, wherein the calculating of the language fluency value includes an operation of applying and then scoring an adjusted score criterion to at least one of a total number of words, a number of words in a first half, a number of words in a second half, a number of letters per word, a number of category changes, a number of words by category, and a number of repeated words.

4. The dementia test method of claim 3, wherein the preset reference value is set differentially for each of test groups classified based on auxiliary information including at least one of gender, age, education level, and a number of people living together.

5. The dementia test method of claim 1, wherein the second test content analysis operation further includes an operation of analyzing a change in a speech style based on the second answer and existing test data of the user terminal, in the case in which the user terminal has a test history, wherein the speech style includes a speech speed and pronunciation accuracy.

6. The dementia test method of claim 1, further including:
    an operation to confirm an intention to conduct a test;
    an auxiliary information collection operation; and
    an operation of classifying a test group based on the auxiliary information.

7. The dementia test method of claim 6,
    wherein the auxiliary information collection operation includes:
    an operation of providing an auxiliary information question asking any one of gender, age, education level, and a number of people living together to the user terminal; and
    acquiring an auxiliary information answer from the user terminal, and
    wherein the operation of classifying the test group includes:

an operation of converting the auxiliary information answer into text data; and an operation of classifying the test group based on the text data.

8. A computer-readable recording medium in which a computer program for executing the dementia test method based on the artificial intelligence telephone call of claim 1 is stored in combination with a computer, which is hardware.

9. A dementia test server based on an artificial intelligence telephone call performing a dementia test based on question and answer using the artificial intelligence telephone call, the server including:

a communication unit communicating with a user terminal to provide an artificial intelligence telephone call, transmitting a question and test result to the user terminal, and receiving an answer from the user terminal;

a dementia test progress unit providing guidance to the user terminal, conducting a first test, which is an initial familiarization test, in order to increase a test subject's understanding of a test progress method, conducting a second test, a main test, used to determine a presence of dementia or a dementia symptom level of the test subject, wherein the first test is conducted by providing a first question for requesting an answer to a first topic to the user terminal for a first time period and acquiring a first answer from the user terminal, and the second test is conducted by providing a second question for requesting an answer to a second topic, different from the first topic, to the user terminal for a second time period, longer than the first time period, and acquiring a second answer from the user terminal; and an analysis unit analyzing content of the first test by calculating an understanding value, which is a value numerically quantifying a degree of the test subject's understanding of the test progress method based on the first answer, and when the understanding value is lower than a preset value, determining that the test subject does not understand the test progress method, and guiding the test progress method without conducting the second test or scheduling a test thereafter, and analyzing content of the second test by converting the second answer into text data, extracting at least one word corresponding to the second topic from the text data, calculating a language fluency value based on at least one word corresponding to the extracted second topic, comparing and analyzing the language fluency value with a preset reference value, and when the language fluency value is lower than the preset reference value, determining that the test subject is a subject for a follow-up test.

10. The dementia test server of claim 9, wherein the first time period is 10 seconds or more and 30 seconds or less, and the second time period is 30 seconds or more and 60 seconds or less.

11. The dementia test server of claim 9, wherein when calculating the language fluency value, the analysis unit is configured to apply and then score an adjusted score criterion to at least one of a total number of words, a number of words in a first half, a number of words in a second half, a number of letters per word, a number of category changes, a number of words by category, and a number of repeated words.

12. The dementia test server of claim 11, wherein the preset reference value is set differentially for each of test groups classified based on auxiliary information including at least one of gender, age, education level, and a number of people living together.

13. The dementia test server of claim 9, wherein when analyzing the content of the second test, the analysis unit is configured to analyze a change in a speech style based on the second answer and existing test data of the user terminal, in the case in which the user terminal has a test history, and wherein the speech style includes a speech speed and pronunciation accuracy.

14. The dementia test server of claim 9, wherein the analysis unit is configured to:

confirm an intention to conduct a test;

collect auxiliary information; and classify a test group based on the auxiliary information.

15. The dementia test server of claim 14, wherein when collecting the auxiliary information, the analysis unit is configured to:

provide an auxiliary information question asking any one of gender, age, education level, and a number of people living together to the user terminal; and acquire an auxiliary information answer from the user terminal, and wherein when classifying the test group, the analysis unit is configured to:

convert the auxiliary information answer into text data; and classify the test group based on the text data.

* * * * *